United States Patent [19]

Rechsteiner

[11] Patent Number: 4,661,100
[45] Date of Patent: Apr. 28, 1987

[54] URINARY RECEPTACLE

[76] Inventor: Jim Rechsteiner, Regentesselaan 30, Hilversum, Netherlands

[21] Appl. No.: 673,339

[22] Filed: Nov. 20, 1984

[30] Foreign Application Priority Data

Dec. 1, 1983 [NL] Netherlands ............................ 8304124

[51] Int. Cl.4 .............................................. A61M 1/00
[52] U.S. Cl. .................................... 604/327; 604/317; 604/318
[58] Field of Search ................................. 604/317–318, 604/327, 333, 322, 56, 82, 87, 89, 90

[56] References Cited

U.S. PATENT DOCUMENTS

| | | | |
|---|---|---|---|
| 911,523 | 2/1909 | Piers | 604/87 |
| 2,917,047 | 12/1959 | Milton | 604/87 |
| 2,954,046 | 9/1960 | Lloyd | 604/113 |
| 3,312,221 | 4/1967 | Overment | 604/317 |
| 3,505,775 | 4/1970 | Anderson et al. | 422/34 |
| 3,818,910 | 6/1974 | Harris | 604/87 |
| 3,918,433 | 11/1975 | Fuisz | 604/317 |
| 4,241,733 | 12/1980 | Langston et al. | 604/322 |
| 4,386,930 | 6/1983 | Cianci | 604/317 |

Primary Examiner—C. Fred Rosenbaum
Assistant Examiner—Gene B. Kartchner
Attorney, Agent, or Firm—John P. Snyder

[57] ABSTRACT

An urinary receptacle having an inlet connection for connection with a feeding duct and an outlet connection that can be closed with at least one container arranged in the receptacle and to be opened from the outside of the receptacle and containing a material having an effect on the urine. The container is made from a fragile synthetic resin, which may be broken to introduce the material into the urine. The material may be a disinfectant or a diagnostic agent, to reveal the presence of protein for example.

4 Claims, 3 Drawing Figures

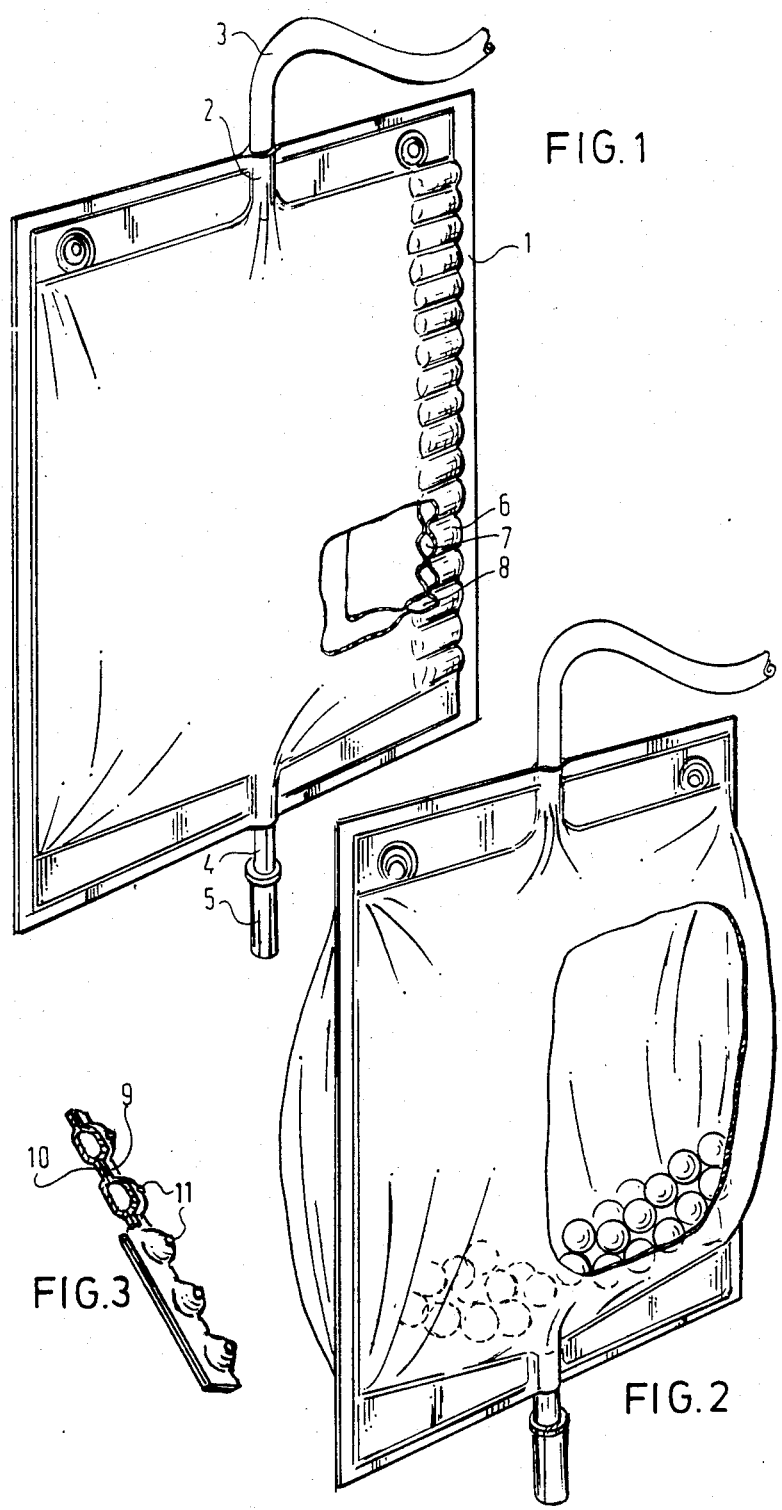

URINARY RECEPTACLE

The invention relates to an urinary receptacle having an inlet connection for connection with a feeding duct and an outlet connection that can be closed with at least one container arranged in the receptacle and to be opened from the outside of the receptacle and containing a material having an effect on the urine.

Such an urinary receptacle is known from No. DE-A-3.118.860.

Such an urinary receptacle is used inter alia in hospitals. The patient is connected through a hose with the urinary receptacle, which has, of course, to be periodically emptied by the hospital staff. By introducing periodically a disinfecting material into the receptacle the increase of bacteria in the receptacle is reduced so that the risk of cystitis of the patient is reduced. This may furthermore be important in emptying the receptacle, since there is a great risk that in emptying the ambience, for example, the nurse's hand might be infected. This is, of course, undesirable in a hospital where the ambience should be as sterile as possible.

An inconvenience of the known device is that dosing is difficult and cannot be checked with respect to the amount of disinfectant really introduced into the receptacle according to need. Therefore, the use of the known device highly depends on the hospital staff. If it is forgotten to pinch the receptacle, no disinfection takes place, which cannot be assessed.

The invention has for its object to provide a solution for this problem. According to the invention this is achieved in that the container is made from fragile material of synthetic resin.

By pinching the container to pieces from the outside disinfecting material is introduced in an apportioned amount into the urinary receptacle. It is visible from the outside whether this has really taken place so that it can be checked in a simple manner whether the addition of the disinfectant has taken place.

Preferably several containers are arranged, for example, in a seam of the receptacle. This has the advantage that the disinfectant can be introduced in doses into the urinary receptacle by pinching one or more containers to pieces.

Therefore, the invention provides a satisfactory dosability together with the possibility of an external check.

It is noted that from U.S. Pat. No. 3,312,221 there is known a receptacle having pellets of disinfecting material. The container is normally not closed and need, therefore, not be opened from the outside. Dosing of the disinfectant is, therefore, not possible.

A further advantage of the invention over the construction of said U.S. patent specification is that disinfection of the contents of the urinary receptacle can take place at the most desirable instant. In order to permit repeated use of the urinary receptacle it is preferred to provide several containers, for example, in the seam of a receptacle. Prior to use and then each time after the receptacle is emptied one of the containers can be opened by pinching the receptacle at the area concerned so that the collected amount of urine comes into contact with the dosed amount of disinfectant. As an alternative a plurality of containers enclosed between relatively sealed layers of synthetic resin may be assembled to form an unit in which an opening is provided in one of the layers for each container. Such an unit can then be inserted into the urinary receptacle through an opening that can be closed, for example, the outlet connection. It is furthermore possible to introduce into the containers a diagnostic means revealing the presence of a substance, for example, protein in the urine by discolouring.

The invention will be explained with reference to the accompanying drawing.

FIG. 1 shows an urinary receptacle embodying the invention.

FIG. 2 shows a different embodiment of the invention, and

FIG. 3 shows a plurality of containers assembled to form a strip-shaped unit.

The receptacle 1 comprises an inlet connection 2 with which a hose 3 is connected for the patent. On the underside the receptacle 1 is provided with an outlet connection 4, which can be closed by means of a closing plug 5. In the seam 6 of the receptacle 1 are arranged containers for example 7,8 embodying the invention. The containers are retained in position by portions of the wall of the receptacle as seen in cross-hatched lines in FIG. 1, these portions being illustrated as formed by conventional heat sealing techniques in a well-known manner. The containers 7,8 are separate from the wall of the receptacle and are made from readily breakable synthetic resin and can be opened from the outside of the receptacle 1 by pinching the receptacle at the area of the container. The containers each have a cavity therewithin and have disinfectant material disposed within such cavity.

As shown in FIG. 2, the containers are loosely arranged in the receptacle.

As an alternative, the containers may be assembled to form a strip-shaped unit consisting of two relatively sealed layers of synthetic resin 9,10, between which the containers are enclosed. For each container an opening 11 is provided in or near one of the layers 9,10. Such a strip can be introduced into the urinary receptacle for example, through the outlet connection 4 that can be closed.

What I claim is:

1. A urinary receptacle for repeated use comprising the combination of a flexible body including a wall defining a chamber for collecting a patient's urine, said chamber having an inlet passage which is continuously open, tubular means connected with the inlet passage and adapted to be connected to a patient for collecting urine from a patient when in use, said chamber also having an outlet passage provided with closing means for sealing the receptacle to allow accumulation of a patient's urine to start a urine collection cycle and for draining the patient's urine to terminate a urine collection cycle, rupturable container means within said receptacle and being separate from said wall, said rupturable container means comprising a plurality of rupturable containers individually and separately retained in position by portions of said wall of said receptacle, each of said containers containing a substance which affects urine within said chamber collected during a urine collection cycle, each of said containers having a cavity therewithin, said substance being disposed within said cavity, whereby, said substance can be released into the chamber by squeezing and rupturing one of said containers through deformation of said body while visually or tactilely verifying such rupture and thereby assuring that said substance has been dispensed within said receptacle.

2. A urinary receptacle for repeated use comprising the combination of a flexible body including a wall defining a chamber for collecting a patient's urine, said chamber having an inlet passage which is continuously open, tubular means connected with the inlet passage and adapted to be connected to a patient for collecting urine from a patient when in use, said chamber also having an outlet passage provided with closing means for sealing the receptacle to allow accumulation of a patient's urine to start a urine collection cycle and for draining the patient's urine to terminate a urine collection cycle, rupturable container means within said receptacle and being separate from said wall, said rupturable container means comprising a plurality of rupturable containers each containing a substance which affects urine within said chamber collected during a urine collection cycle, each of said containers having a cavity therewithin, said substance being disposed within said cavity, and two layers of material sealed to one another and individually enclosing each of said containers, at least one of said layers having openings therein to allow escape of said substance from each of said containers, whereby, said substance can be released into the chamber by squeezing and rupturing one of said containers through deformation of said body while visually or tactilely verifying such rupture and thereby assuring that said substance has been dispensed within said receptacle.

3. A urinary receptacle as defined in any one of claims 1-2 wherein said substance is a disinfectant.

4. A urinary receptacle as defined in any one of claims 1-2 wherein said substance is a diagnostic agent which reveals, through discoloration, the presence of material such as protein.

* * * * *